United States Patent
Liou et al.

(10) Patent No.: US 9,533,018 B2
(45) Date of Patent: Jan. 3, 2017

(54) **METHOD OF PROCESSING *ANTRODIA CINNAMOMEA***

(71) Applicant: HAN SHENG BIOTECH CO., LTD., Pingtung County (TW)

(72) Inventors: Shorong-Shii Liou, Pingtung County (TW); I-Min Liu, Pingtung County (TW)

(73) Assignee: HAN SHENG BIOTECH CO., LTD, Pingtung County (TW)

( * ) Notice: Subject to any disclaimer, the term of this patent is extended or adjusted under 35 U.S.C. 154(b) by 33 days.

(21) Appl. No.: 14/725,206

(22) Filed: May 29, 2015

(65) Prior Publication Data
US 2016/0346338 A1  Dec. 1, 2016

(51) Int. Cl.
*A61K 36/07* (2006.01)
*A61K 36/09* (2006.01)
*A61K 31/56* (2006.01)
*A61K 31/575* (2006.01)

(52) U.S. Cl.
CPC .............. *A61K 36/07* (2013.01); *A61K 31/575* (2013.01)

(58) Field of Classification Search
None
See application file for complete search history.

(56) References Cited

FOREIGN PATENT DOCUMENTS

TW          I471161          2/2015

*Primary Examiner* — Chris R Tate
*Assistant Examiner* — Russell Fiebig
(74) *Attorney, Agent, or Firm* — WPAT, P.C., Intellectual Property Attorneys; Anthony King

(57) ABSTRACT

The invention discloses a method of processing *Antrodia cinnamomea* for producing a processed sample of *Antrodia cinnamomea*, which easily releases antcin K in a following extraction process. The method includes the steps of: soaking a raw sample of *Antrodia cinnamomea* with a processing reagent comprising 25-83.3 wt % of rice vinegar and 16.7-75 wt % of yellow wine at 22-28° C. for 22-26 hours; and steaming the soaked product at 1-3 $kg/cm^2$, 110-150° C. for 10-50 minutes.

7 Claims, 5 Drawing Sheets

METHOD OF PROCESSING *ANTRODIA CINNAMOMEA*

BACKGROUND OF THE INVENTION

1. Field of the Invention

The present invention generally relates to a method of processing *Antrodia cinnamomea* and, more particularly, to a method of processing *Antrodia cinnamomea* for producing a processed sample of *Antrodia cinnamomea*, which easily releases antcin K in a following extraction process.

2. Description of the Related Art

*Antrodia cinnamomea*, a precious traditional Chinese medicine in Taiwan, grows only on inner rotten walls of hollow materials from a conserving species of *Cinnamomum kanehirai*. Wild species *Antrodia cinnamomea* is rich in triterpenoids, which are believed to possess effects such as anti-tumor, liver-protective, anti-dotal, anti-high blood lipid and pressure and immuno-modulating activities.

Antcin K (as shown in FIG. 1), one of particular triterpenoids of *Antrodia cinnamomea*, belongs to ergosterols and shows a similar structure with cholesterol. In this way, antcin K is easy to interfere with the biochemical paths of metabolism of cholesterol and generation of cell membrane, and therefore plays a critical role in cell cycle and physiological metabolism. Also, it is reported that antcin K can lead to apoptosis of liver cancer cells, thereby being dramatically effective in treating of liver cancer.

A conventional method of processing *Antrodia cinnamomea* is recited in Taiwan patent No. 1471161, which soaks a raw sample of *Antrodia cinnamomea* with a salt solution, followed by steaming the soaked sample to obtain a conventional processed sample. The conventional processed sample can be further extracted to obtain an extract with an increased dehydrosulphurenic acid level. As such, the obtained extract can be applied to manufacturing the medication for pancreas cancer and/or acute myeloid leukemia.

However, the said obtained extract has a low antcin K level, and therefore shows a decreased effect on treating liver cancer. In light of this, it is necessary to provide a method of processing *Antrodia cinnamomea*.

SUMMARY OF THE INVENTION

It is therefore the objective of this invention to provide a method of processing *Antrodia cinnamomea* for producing a processed sample of *Antrodia cinnamomea*, which easily releases antcin K in a following extraction process.

One embodiment of the invention discloses a method of processing *Antrodia cinnamomea* including the steps of: soaking a raw sample of *Antrodia cinnamomea* with a processing reagent comprising 25-83.3 wt % of rice vinegar and 16.7-75 wt % of yellow wine at 22-28° C. for 22-26 hours; and steaming the soaked product at 1-3 kg/cm$^2$, 110-150° C. for 10-50 minutes.

In a preferred form shown, the processing reagent comprises 75 wt % of rice vinegar and 25 wt % of yellow wine.

In a preferred form shown, the method further includes the step of: before soaking the raw sample of *Antrodia cinnamomea* with the processing reagent, removing impurities adhering on surfaces of the raw sample of *Antrodia cinnamomea*.

In a preferred form shown, the raw sample of *Antrodia cinnamomea* is soaked with the processing reagent for 24 hours.

In a preferred form shown, the soaked product is steamed at 1 kg/cm$^2$, 121° C. for 30 minutes.

In a preferred form shown, 500 grams of the raw sample of *Antrodia cinnamomea* is soaked with 100 mL of the processing reagent.

In a preferred form shown, the raw sample of *Antrodia cinnamomea* is a fruit body of *Antrodia cinnamomea*.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

Figure 1:
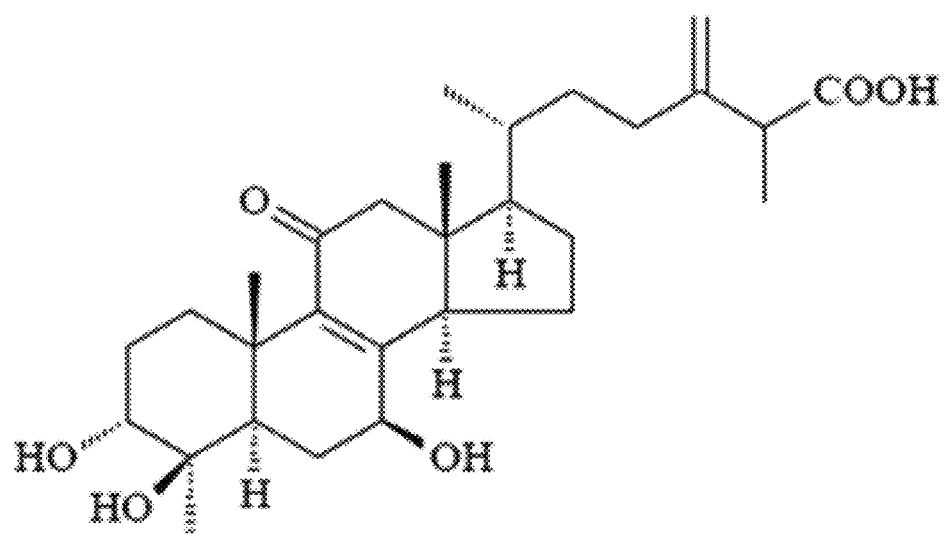
FIG. 1 depicts chemical structure of antcin K.

In the various figures of the drawings, the same numerals designate the same or similar parts. Furthermore, when the term "first", "second", "third", "fourth", "inner", "outer", "top", "bottom" and similar terms are used hereinafter, it should be understood that these terms refer only to the structure shown in the drawings as it would appear to a person viewing the drawings, and are utilized only to facilitate describing the invention.

DETAILED DESCRIPTION OF THE INVENTION

A method of processing *Antrodia cinnamomea* according to the present invention includes the steps of: soaking a raw sample of *Antrodia cinnamomea* with a processing reagent; and steaming the soaked product to obtain a processed sample of *Antrodia cinnamomea*.

Specifically, the raw sample indicates a dried one. In the embodiment, a fruit body rich in triterpenoids is selected to be the raw sample. More particularly, impurities adhering on the surfaces of the fruit body can be removed before soaking the raw sample with the processing reagent.

Further, the processing reagent is a mixture containing rice vinegar and yellow wine, especially as the mixture containing 25-83.3 wt % of rice vinegar and 16.7-75 wt % of yellow wine.

The raw sample is then soaked with the processing reagent at 22-28° C. for 22-26 hours to obtain the soaked product. In this embodiment, the soaking process is carried out using a sealed container to prevent from contamination of the impurities. Therefore, the processing reagent can penetrate into the raw sample to form the soaked product. For example, in this embodiment, 500 grams of the raw sample is soaked with 100 mL of the processing reagent for 24 hours.

The soaked product is then steamed at 1-3 kg/cm$^2$, 110-150° C. for 10-50 minutes and the obtained processed sample has a color of reddish black. In this embodiment, a pressure cooker set at 1 kg/cm$^2$ and 121° C. is used for steaming the soaked product for 30 minutes. It is noteworthy that if the steaming temperature is lower than 110° C., the efficiency in the following extraction will be poor, while if the steaming temperature is higher than 150° C., the active ingredients will be possibly destroyed.

In order to evaluate the obtained processed sample can easily release antcin K in a following extraction process, 95% ethanol is used as an extractant to carried out the extraction process. HPLC analysis is then carried out to quantify antcin K level of the obtained extract.

The raw sample is soaked with the processing reagent shown in TABLE 1, followed by steaming to obtain the processed sample of groups A1-A6, respectively. The processed sample (5 grams) is then supersonic extracted with 95% ethanol (600 mL) to obtain the extract of groups A1-A6, respectively (40 KHz, extraction thrice for 8 hours each times). Moreover, an extract extracted from the raw material is used as a control (group A0).

TABLE 1

Figure 2A:
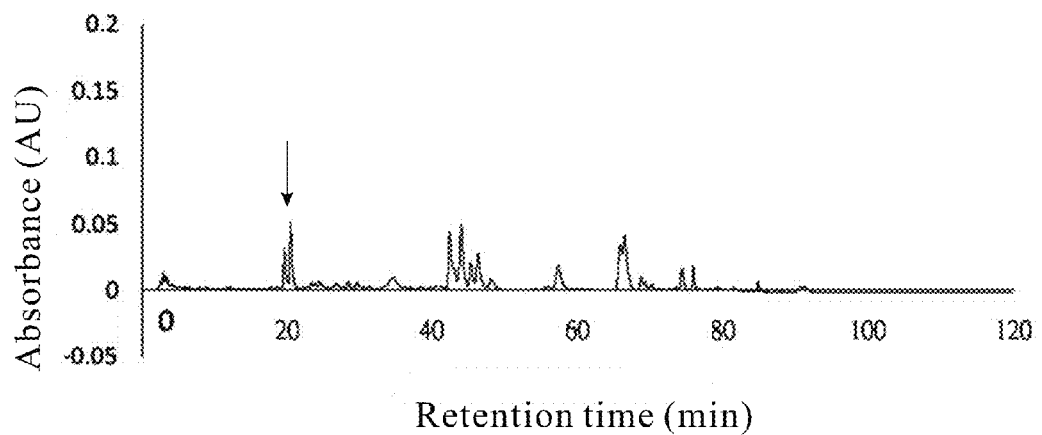
FIG. 2*a* depicts antcin K level of an extract in group A0.
Figure 2B:
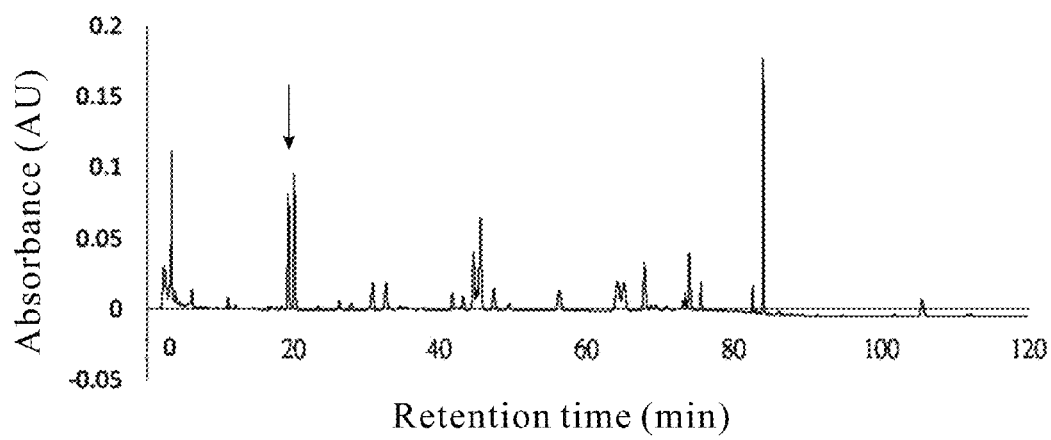
FIG. 2*b* depicts antcin K level of an extract in group A1.
Figure 2C:
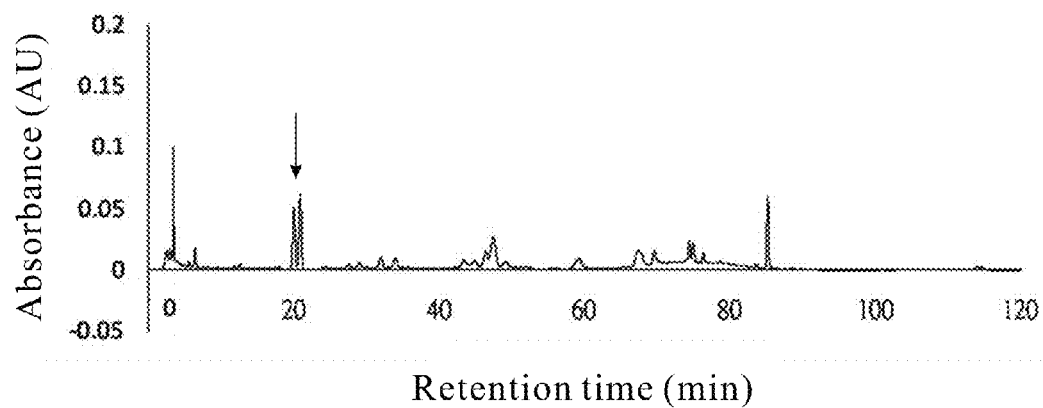
FIG. 2*c* depicts antcin K level of an extract in group A2.
Figure 2D:
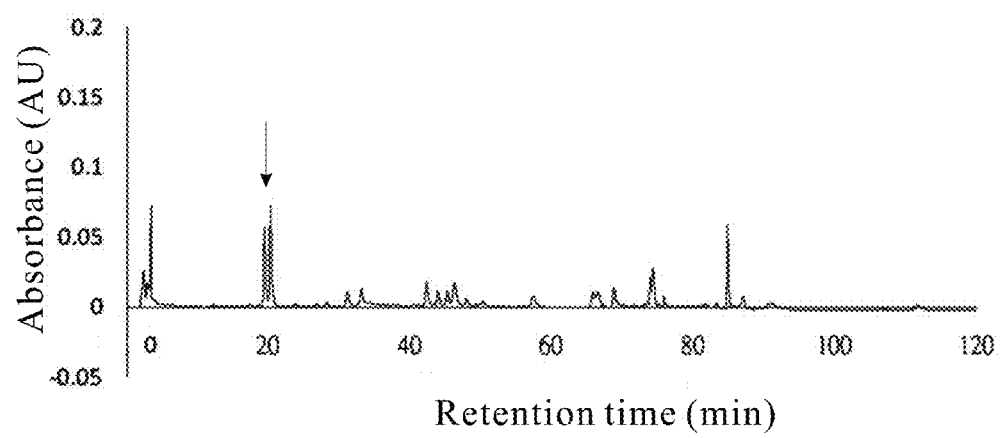
FIG. 2*d* depicts antcin K level of an extract in group A3.
Figure 2E:
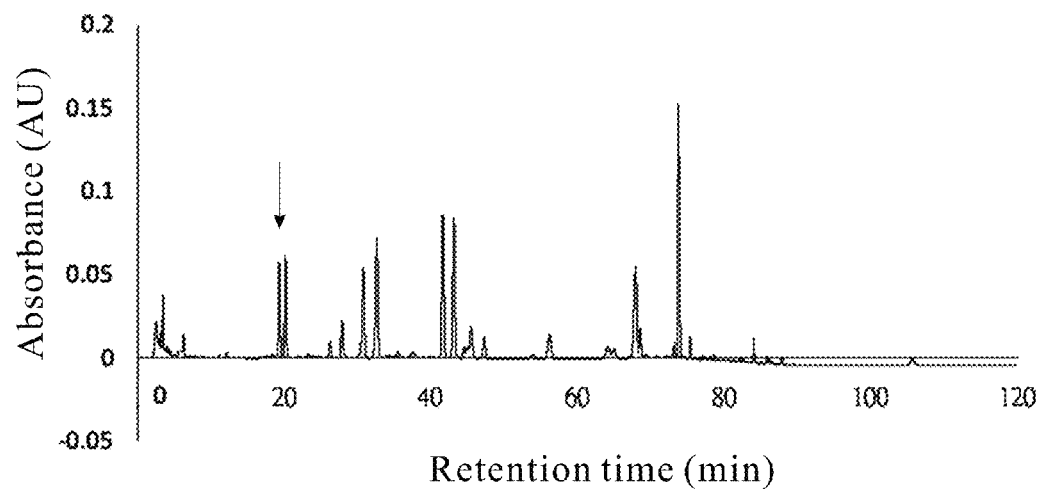
FIG. 2*e* depicts antcin K level of an extract in group A4.
Figure 2F:
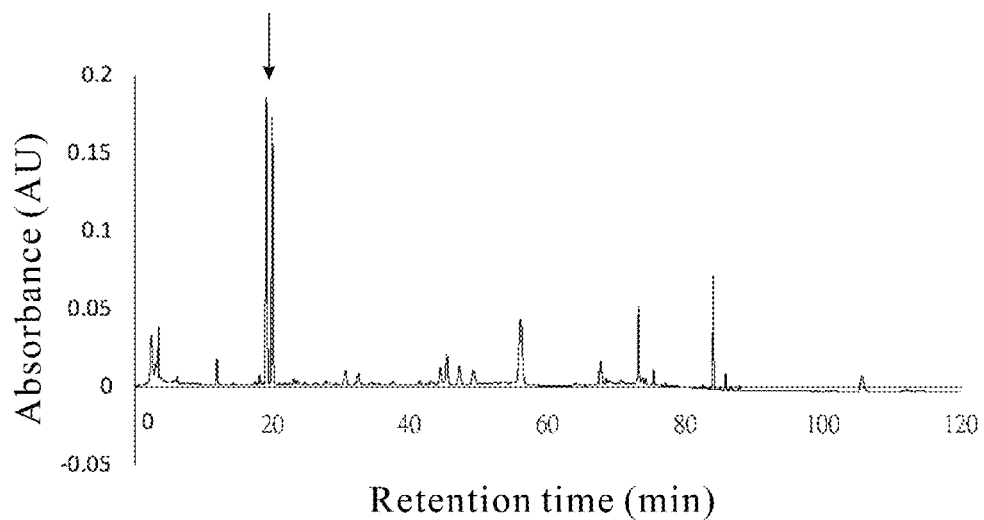
FIG. 2*f* depicts antcin K level of an extract in group A5.
Figure 2G:
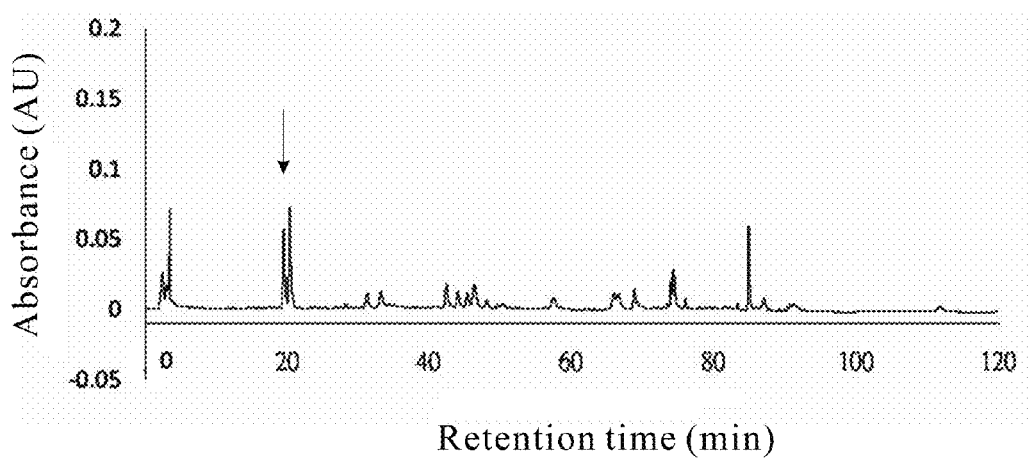
FIG. 2*g* depicts antcin K level of an extract in group A6.

| Groups | Formula of processing reagent (wt %) | | Result |
| --- | --- | --- | --- |
| | Rice vinegar | Yellow wine | |
| A0 | 0 | 0 | FIG. 2a & TABLE 3 |
| A1 | 25 | 75 | FIG. 2b & TABLE 3 |
| A2 | 33.3 | 66.7 | FIG. 2c & TABLE 3 |
| A3 | 50 | 50 | FIG. 2d & TABLE 3 |
| A4 | 66.7 | 33.3 | FIG. 2e & TABLE 3 |
| A5 | 75 | 25 | FIG. 2f & TABLE 3 |
| A6 | 83.3 | 16.7 | FIG. 2g & TABLE 3 |

For analyzing triterpenes, the extract (0.2 grams) is mixed with methanol (5 mL), followed by ultrasonic vibration for 15 minutes and centrifugation at 3,000 rpm for 10 minutes. The obtained supernatant is then dried using a 100° C. water bath.

Further, Purospher STAR (purchased from Merck) RP-18e (5 μm) 250 mm×4.6 mm column is used. A mobile phase for eluting triterpenes is shown in TABLE 2 with a flow rate of 1 mL/min. The peak of antcin K shown in 254 nm is shown as the arrow in FIGS. 2a-2g.

TABLE 2

| Stages | Elution time (min) | Formula of mobile phase (wt %) | |
| --- | --- | --- | --- |
| | | Acetonitrile | 0.085% phosphoric acid |
| a | 0 | 40 | 60 |
| b | 30 | 47 | 53 |
| c | 50 | 47 | 53 |
| d | 100 | 100 | 0 |
| e | 120 | 100 | 0 |

Referring to FIGS. 2a-2g, the peak areas of triterpenes are analyzed and recorded in TABLE 3.

TABLE 3

| Active ingredient | Retention time (min) | Peak area (%) | | | |
| --- | --- | --- | --- | --- | --- |
| | | A0 | A1 | A2 | A3 |
| Antcin K | 19.853 | 4.212 | 9.619 | 6.580 | 8.627 |
| | 20.727 | 7.232 | 11.962 | 7.831 | 11.79 |
| Phenols | 28.767 | 1.125 | 1.028 | 2.265 | 0.718 |
| Antcin C | 42.913 | 9.876 | 2.515 | 1.336 | 3.813 |
| | 44.327 | 10.879 | 2.186 | 1.253 | 2.643 |
| Zhankuic acid C | 45.907 | 3.702 | 4.095 | 4.382 | 2.322 |
| | 46.927 | 6.284 | 9.767 | 7.961 | 5.638 |
| Dehydro-sulphurenic acid | 58.253 | 6.386 | 4.125 | 2.420 | 2.403 |
| Zhankuic acid A | 64.033 | 7.178 | 6.077 | 4.509 | 2.863 |
| | 64.867 | 11.15 | 5.261 | 3.668 | 3.162 |
| Antcin A | 74.480 | 2.839 | 2.472 | 3.997 | 5.661 |
| Dehydro-eburicoic acid | 84.700 | 0.675 | 8.358 | 9.206 | 7.046 |

| Active ingredient | Retention time (min) | Peak area (%) | | |
| --- | --- | --- | --- | --- |
| | | A4 | A5 | A6 |
| Antcin K | 19.853 | 8.022 | 20.200 | 10.859 |
| | 20.727 | 10.122 | 19.008 | 13.957 |
| Phenols | 28.767 | 0.017 | 1.467 | 0.671 |
| Antcin C | 42.913 | 0.654 | 0.340 | 2.868 |
| | 44.327 | 0.376 | 0.237 | 4.225 |
| Zhankuic acid C | 45.907 | 1.534 | 1.690 | 2.114 |
| | 46.927 | 5.012 | 3.164 | 4.070 |
| Dehydro-sulphurenic acid | 58.253 | 5.699 | 10.640 | 2.628 |
| Zhankuic acid A | 64.033 | 2.766 | 0.106 | 2.523 |
| | 64.867 | 2.312 | 0.027 | 1.983 |
| Antcin A | 74.480 | 1.625 | 4.137 | 1.601 |
| Dehydro-eburicoic acid | 84.700 | 6.112 | 5.158 | 6.732 |

Referring to FIGS. 2a-2g and TABLE 3, compared to antcin K level of the extract in group A0, antcin K level of the extracts in groups A1-A6 shows significant increase, especially antcin K level of the extract in group A5, showing approximately 2-4-fold increase. That is, the method of processing *Antrodia cinnamomea* according to the present invention can be used for producing the processed sample of *Antrodia cinnamomea*, which easily releases antcin K in a following extraction process.

Accordingly, by carrying out the method of processing *Antrodia cinnamomea*, the obtained processed sample can easily release antcin K in the following extraction process. Therefore, the extract can be applied to manufacturing a medication for liver cancer, thereby effectively decreasing tumor burden and inhibiting liver cancer progression.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method of processing *Antrodia cinnamomea* to produce an extract of *Antrodia cinnamomea* with a high content of antcin K comprising the steps of:
   (a) soaking a sample of raw *Androdia cinnamomea* in a processing reagent comprising 25-83.3 wt % of rice vinegar and 16.7-75 wt % of yellow wine (*Huangjiu*) at 22-28° C. for 22-26 hours to obtain a soaked product,
   (b) steaming the soaked product of step (a) for 10-50 minutes at 110-150° C. at 1-3 kg/cm$^2$ to produce a steamed product,
   (c) extracting the steamed product of step (b) with an extraction solvent to produce the extract of *Antrodia cinnamomea* with a high content of antcin K.

2. The method of processing *Antrodia cinnamomea* as claimed in claim 1, wherein the processing reagent comprises 75 wt % of rice vinegar and 25 wt % of yellow wine.

3. The method of processing *Antrodia cinnamomea* as claimed in claim 1, further comprising the step of:
    removing impurities adhering on surfaces of the raw sample of *Antrodia cinnamomea* prior to soaking step (a).

4. The method of processing *Antrodia cinnamomea* as claimed in claim 1, wherein the raw sample of *Antrodia cinnamomea* is soaked with the processing reagent for 24 hours.

5. The method of processing *Antrodia cinnamomea* as claimed in claim 1, wherein the soaked product is steamed at 1 kg/cm$^2$, 121° C. for 30 minutes.

6. The method of processing *Antrodia cinnamomea* as claimed in claim 1, wherein 500 grams of the raw sample of *Antrodia cinnamomea* is soaked with 100 mL of the processing reagent.

7. The method of processing *Antrodia cinnamomea* as claimed in claim 1, wherein the raw sample of *Antrodia cinnamomea* is a fruit body of *Antrodia cinnamomea*.

\* \* \* \* \*